United States Patent [19]

Artzt et al.

[11] 4,246,748
[45] Jan. 27, 1981

[54] METHOD AND APPARATUS FOR DETECTING THE FAULTY OPERATION OF SPINNING UNITS OPEN-END SPINNING MACHINES

[75] Inventors: Peter Artzt, Pfullingen; Gerhard Egbers; Rolf Guse, both of Reutlingen; Sohrab Tabibi, Pfullingen, all of Fed. Rep. of Germany

[73] Assignee: Schubert & Salzer, Ingolstadt, Fed. Rep. of Germany

[21] Appl. No.: 767,998

[22] Filed: Feb. 11, 1977

[30] Foreign Application Priority Data

Feb. 13, 1976 [DE] Fed. Rep. of Germany ....... 2605736

[51] Int. Cl.³ .................... D01H 13/22; D01H 13/32; G06F 15/46
[52] U.S. Cl. .......................................... 57/265; 57/81; 57/264; 364/470; 364/552
[58] Field of Search ...................... 57/81, 34 R, 58.89, 57/58.95, 264, 265; 340/259; 364/470, 552, 554, 563

[56] References Cited

U.S. PATENT DOCUMENTS

| 4,007,457 | 2/1977 | Aeppli | 57/34 R |
| 4,060,965 | 12/1977 | Schwartz | 57/34 R |

*Primary Examiner*—John Petrakes
*Attorney, Agent, or Firm*—Bailey, Dority & Flint

[57] ABSTRACT

A method and apparatus of detecting faulty operations of spinning units of an open-end spinning machine by monitoring the faults appearing in the yarn being produced by the machine and generating a fault signal responsive thereto. Another speed responsive signal is produced responsive to the speed that the yarn is being delivered from the spinning compartment of the machine. The fault signal is fed to a variable gain amplifier which has its gain controlled by the speed responsive signal. The signal produced by the amplifier is then differentiated, shaped, and integrated. The integrated signal is, in turn, compared with a threshold value for determining when the faults in the yarn exceed a predetermined level.

6 Claims, 2 Drawing Figures

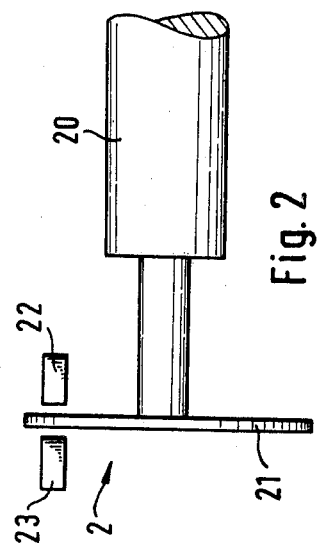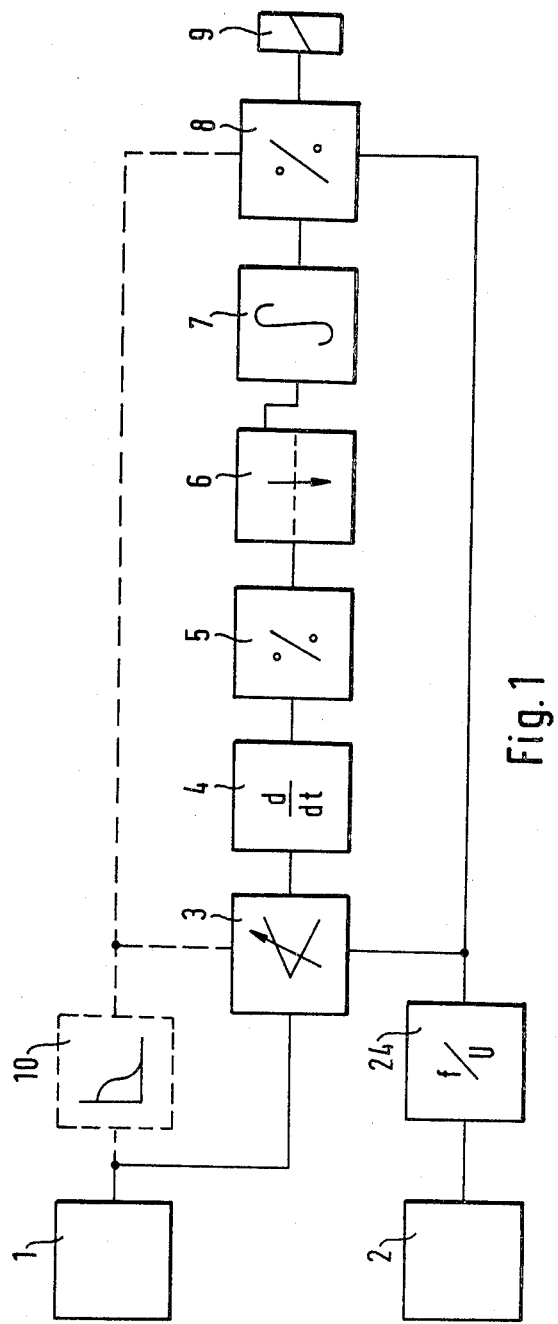

METHOD AND APPARATUS FOR DETECTING THE FAULTY OPERATION OF SPINNING UNITS OPEN-END SPINNING MACHINES

BACKGROUND OF THE INVENTION

It is generally known in the spinning industry that, apart from the irregularities in the yarn, which have the most varied amplitudes, periodic deviations occur which are later clearly visible in the yarn (yarn conversion table) and also in the woven fabric as a result of their position side by side. This phenomenon is generally known as the moire effect. The causes of such periodic faults in the yarn originate from the processing, during which disturbances occur periodically. In a ring spinning machine, for example, such disturbances may result from drawing rollers oscillating. In rotor spinning, such disturbances appear particularly strikingly as a result of deposits in the rotor. Because it is known what generally causes the periodic disturbances, conclusions regarding the source of disturbance can be drawn from a yarn unevenness diagram.

In open-end spinning, with regard to moire detection, it is known that the visible spacing of thick places appearing on the yarn appear according to the circumference of the rotor. The difficulty of detection, however, lies in the fact that the delivery speed is variable and so the moire frequency is likewise variable.

It is true that it is possible to check a yarn production afterwards by means of random samples with the aid of a spectograph (Uster), for whether such a moire effect has occurred or not; nevertheless, serious damage results because the production has already taken place, and, in any case, a relatively large amount of faulty yarn may have been produced depending on the frequency of the checking.

It is true that it is already known to detect the point of the disturbance directly and immediately by monitoring individual spindles so as to avoid a large faulty production (DT-OS 2.409.882 corresponding to U.S. Pat. No. 4,007,457 ). According to the earlier proposal, this is effected in that an electric signal is produced by measuring the yarn cross-section or yarn diameter, which signal is subjected to an evaluation by means of at least one non-linear correction member.

In order to detect periodic faults in the spun yarn, it is necessary, in this case, to convey the signal originating from a monitored yarn through electric filters which are adjusted to the expected repetition frequency of these faults, hereinafter termed moire frequency, and a detector has to be present at each spinning station. Since the delivery speed of the spun thread is variable, either narrow-band filters have to be used, which are variable in their midband frequency, which leads to considerable costs, or very wide-band filters have to be used so that the moire frequency is transmitted thereby even with different yarn-delivery speeds. It is true that in the latter case, the costs for the circuits are reduced somewhat, but the wide-band nature of the filters means that a considerable proportion of the frequencies of the normal irregularity in the spun yarn can pass. A moire effect is therefore only detected, when using wide-band filters, if it stands out very distinctly from the normal irregularity of the thread.

SUMMARY OF THE INVENTION

According to the invention, this problem is solved in that the yarn signal obtained is differentiated and subjected to pulse shaping, after which the shaped pulse train is integrated and compared with a predetermined threshold value. The range of yarn counts which can be monitored is extended as a result of the fact that the processing of the thread signal is kept independent of the thread-delivery speed what is meant by independent of the thread delivery speed is that the signal produced by a yarn sensor is amplified before differentiating and the amplification is influenced by a second signal which is derived from the yarn delivery speed. The apparatus for carrying out the method, which is equipped with a measurement receiver is characterized by a differentiator, a comparator, a pulse shaper, an integrator, and a second comparator. The amplitude of the yarn signal to be differentiated is kept independent of the thread-delivery speed by a means of perforated disc or a slotted disc, a frequency-voltage converter and a variable-gain amplifier.

Accordingly, it is an object of the present invention to provide a method and apparatus for determining when components of an open-end spinning machine are not functioning properly.

Another important object of the present invention is to provide a method and apparatus for monitoring the yarn being produced by an open-end spinning machine for detecting the faulty operations of the spinning units, and in particular, the spinning compartment.

Still another important object of the present invention is to provide a method and apparatus which renders possible, in a simple manner, a reliable detection of periodically, reoccurring faults in spun yarn, and hence, faulty operation of the spinning unit of open-end spinning machines.

These and other objects and advantages of the invention will become apparent upon reference to the following specification, attendant claims and drawings.

BRIEF DESCRIPTION OF THE DRAWING

FIG. 1 is a block circuit diagram of the apparatus constructed in accordance with the present invention; and FIG. 2 is an elevational view illustrating an apparatus for measuring the yarn-delivery speed.

DESCRIPTION OF A PREFERRED EMBODIMENT

The apparatus shown in FIG. 1 contains a measurement receiver 1 which converts a measured signal obtained from a sensor that monitors the yarn mass into an electric signal which is hereinafter termed the yarn signal. The measurement receiver 1, which is not illustrated in detail, comprises two parallel coils, in the stray field of which there can be moved a thread sensor which is constructed, for example, in the form of a plate-spring gripped at one side and the natural frequency of which is lower than the lowest rotational frequency of the rotor of the open-end spinning apparatus and which exerts a pressure on the spun yarn in the region between the rotor and the yarn-winding point. Such an arrangement permits the yarn mass to be measured by means of the yarn tension produced by the centrifugal force action on the yarn. A measured signal is produced therefrom. Since this is known a more detailed explanation is not required. The measurement of the yarn mass to produce the yarn signal is preferred. Instead of measuring the yarn mass, however, the yarn diameter or yarn cross-section may also be measured if desired by means of well-known devices and the measured quantity obtained be converted into an electric signal.

The thread signal originating from the measurement receiver 1 is then subjected to differentiation, by means of which a moire effect which has occurred is selected. The selecting of the moire effect by differentiation of the yarn signal, that is to say without using selective filters, is rendered possible by the feature that the fluctuations in mass in the spun yarn which occur with the moire effect, in contrast to normal fluctuations in mass, appear with a relatively steep ascending flank. Since the apparatus is intended to be used for a wide range of yarn counts, however, the yarn signal is not differentiated immediately after leaving the measurement receiver 1, but is first supplied to a variable gain amplifier 3. At the same time, a second signal is supplied to the amplifier 3, which is derived from the yarn delivery speed. The signal generator 2 which produces this second signal contains a preforated disc 21 which is secured to the yarn-delivery roller 20 and with which there is associated a light source 22 and a photoelectric cell 23 (FIG. 2). Naturally, however, other pulse generators may be used, for example a slotted disc with associated magnetic receiver. The frequency of the pulse train thus produced is converted into a voltage by a frequency-voltage converter 24 which is electrically connected to the amplifier 3. In this manner, the gain of the amplifier 3 is adjusted depending on the yarn delivery speed and the further signal process is independent of the yarn-delivery speed and of the yarn count.

Another possibility of keeping the processing of the yarn signal independent of the yarn count consists in that the yarn signal originating from the measurement receiver 1 is supplied on the one hand to the amplifier 3 and on the other hand to an averaging device 10. The signal passing from the averaging device 10 to the amplifier 3 now serves to adjust the gain of the amplifier 3 depending on the average amplitude of the yarn signal. This second possibility of influencing the gain of the amplifier 3 is represented by broken lines in FIG. 1.

The signal leaving the amplifier 3 is differentiated and subjected to a pulse shaping. For this purpose, the amplifier 3 is followed by a differentiator 4 and a comparator 5, which is followed by a monostable multivibrator 6 which acts as a pulse shaper. A Schmitt trigger may, however, easily be used as a pulse shaper. As a result of the introduction of the differentiator 4 into the circuit, the signal can be discriminated with regard to the edge steepness of fluctuations in mass by means of the comparator 5. The monostable multivibrator 6 lengthens the pulses formed in the comparator 5, which pulses are then integrated in an integrator 7. With regular repetition of the pulses, as is the case upon the appearance of a moire effect in the yarn, the integration value rises steadily and ultimately exceeds a threshold value in a second comparator 8 which follows the integrator 7. The threshold value in the comparator 8 may appropriately be derived from the yarn-delivery speed. Accordingly, the comparator 8 is electrically connected to the frequency-voltage converter 24. The threshold value can also be derived from the average amplitude of the yarn signal. In this case the signal formed in the averaging device 10 is supplied to the comparator 8 (broken line). There is likewise the possibility of adjusting the threshold value in the comparator 8 by hand.

When the threshold value is exceeded, the comparator 8 delivers a pulse to a component characterized, for example, by a switch or relay 9, which can be used to switch off the spinning station or to actuate an indicator device.

While a preferred embodiment of the invention has been described using specific terms, such description is for illustrative purposes only, and it is to be understood that changes and variations may be made without departing from the spirit or scope of the following claims.

What is claimed is:

1. A method of detecting faulty operation of spinning units of open-end spinning machine by monitoring the faults appearing in the yarn being produced on said spinning machine, wherein a sensor is positioned between a spinning compartment and a package receiving said yarn generating an electrical signal corresponding to the faults in said yarn, said method comprising the following steps:
    (a) differentiating said electrical signal produced by said yarn sensor producing pulses corresponding to the faults in said yarn,
    (b) shaping said pulses with a pulse shaping circuit,
    (c) integrating said shaped pulses producing an integrated signal, and
    (d) comparing said integrated signal with a predetermined threshold value for producing a signal indicating when the faults in said yarn exceed a predetermined level.

2. The method as set forth in claim 1 wherein said signal produced by said yarn sensor is amplified before differentiating and the amplification is influenced by a second signal which is derived from the yarn delivery speed.

3. The method as set forth in claim 1 wherein said yarn signal is generated by measuring the tension in said yarn which varies according to the mass of the yarn.

4. An apparatus for detecting faulty operation of spinning units of an open-end spinning machine by monitoring faults appearing in the yarn being produced on said spinning machine as it is fed from a spinning compartment to a package, said apparatus comprising:
    (a) means for monitoring said yarn as it is fed from said spinning compartment to said package and generating an electrical signal responsive to faults occurring in said yarn,
    (b) means for differentiating said electrical signal producing pulses corresponding to the faults appearing in said yarn,
    (c) means for shaping said pulses,
    (d) means for integrating said shaped pulses producing an integrated signal, and
    (e) means for generating a threshold signal, and
    (f) means for comparing said integrated signal with said threshold signal and generating a signal when said integrated signal exceeds said threshold signal.

5. The apparatus as set forth in claim 4 further comprising:
    (a) a variable-gain amplifier interposed between said monitoring means and said differentiating means for amplifying said electrical signal prior to said electrical signal being fed to said differentiating means, and
    (b) means for varying the gain of said variable gain amplifier responsive to the speed of delivery of said yarn from said spinning compartment.

6. The apparatus as set forth in claim 5 wherein means for varying the gain of said variable-gain amplifier responsive to the speed of delivery of yarn from said spinning compartment comprises:

(a) a yarn delivery roller,
(b) means for generating a frequency signal corresponding to the speed of rotation of said delivery roller, and
(c) a frequency-to-voltage converter means converting said frequency signal to a voltage and applying said voltage to said variable gain amplifier for controlling the gain thereof.

* * * * *